(12) United States Patent
Chinnathambi et al.

(10) Patent No.: US 11,040,994 B2
(45) Date of Patent: Jun. 22, 2021

(54) COBALT COMPLEXES, PROCESS FOR PREPARATION AND USE THEREOF

(71) Applicant: COUNCIL OF SCIENTIFIC AND INDUSTRIAL RESEARCH, New Delhi (IN)

(72) Inventors: Subashchandrabose Chinnathambi, Pune (IN); Ekambaram Balaraman, Pune (IN); Nalini Vijay Gorantla, Pune (IN); Siba Prasad Midya, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/620,125

(22) PCT Filed: Jun. 6, 2018

(86) PCT No.: PCT/IN2018/050366
§ 371 (c)(1),
(2) Date: Dec. 6, 2019

(87) PCT Pub. No.: WO2018/225087
PCT Pub. Date: Dec. 13, 2018

(65) Prior Publication Data
US 2020/0223880 A1 Jul. 16, 2020

(30) Foreign Application Priority Data
Jun. 6, 2017 (IN) .............................. 201711019807

(51) Int. Cl.
*C07F 15/06* (2006.01)
*A61P 25/28* (2006.01)

(52) U.S. Cl.
CPC ............ *C07F 15/065* (2013.01); *A61P 25/28* (2018.01)

(58) Field of Classification Search
CPC ................................ C07F 15/065; A61P 25/28
See application file for complete search history.

(56) References Cited

U.S. PATENT DOCUMENTS

| | | |
|---|---|---|
| 2014/0088029 A1 | 3/2014 | Sugimoto et al. |
| 2015/0266838 A1 | 9/2015 | Reed et al. |
| 2016/0264535 A1 | 9/2016 | Reed et al. |
| 2016/0318963 A1 | 11/2016 | Chirik et al. |

FOREIGN PATENT DOCUMENTS

| | | |
|---|---|---|
| EP | 2698368 A1 | 2/2014 |
| JP | 4651111 | 3/2011 |
| WO | WO2014/031873 A2 | 2/2014 |
| WO | WO2015/089119 A1 | 6/2015 |
| WO | WO-2015089119 A1 * | 6/2015 ............ C07F 15/065 |

OTHER PUBLICATIONS

Oct. 1, 2018 International Search Report and Written Opinion in connection with PCT/IN2018/050366.
Owen T. Summerscales et al., "Synthesis and Reactivity Studies of Square Planner Diamido-Pyridine Complexes Based on Earth-Abundant First Row Transition Elements", Inorganic Chemistry (Jul. 2015), vol. 54, pp. 6885-6890.
George R. Newkome et al., "Multidentate ligands containing a 2,2'-bipyridine and/or Pyridine moieties: structural aspects of their octahedral and pentagonal-bipyramidal complexes", Inorganic Chemistry (Aug. 1984), vol. 23, pp. 2400-2408.
M M Mahajan & Gurdev Singh, "Five coordinate complexes of 2,6-bis(N, N-diethylaminomethyl) pyridine with Co (II), Ni (II) and Cu (II)", Indian Journal of Chemistry, (Jan. 1990), vol. 29, pp. 1222-1224.
Satoru Karasawa et al., "Formation of monometallic single-molecule magnets with an $S_{total}$ value of 3/2 in diluted frozen solution", Dalton Transactions, (Jan. 2008), No. 11, pp. 1418-1420.
Arnold M. Raitsimring et al., "Supporting Information for Gd+3 complexes as potential Spin label for high field pulsed EPR distance measurements", J. Am. Chem. Soc., (Oct. 2007), 129 (46), pp. S1-S22.
Jeffrey S. Derrick et al., "Mechanistic Insights into Tunable Metal-Mediated Hydrolysis of Amyloid-[beta] Peptides", Journal of the American Chemical Society, (Jan. 2017), vol. 139, pp. 2234-2244.

(Continued)

*Primary Examiner* — Yong L Chu
(74) *Attorney, Agent, or Firm* — Cooper & Dunham LLP

(57) ABSTRACT

The present invention discloses a cobalt compound of formula (I), a process for the preparation and use thereof. The present invention further relates to a pharmaceutical composition and a method inhibition of Tau Aggregation in a subject in need thereof using compound of formula (I).

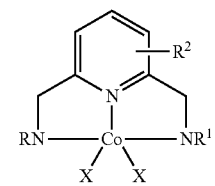

9 Claims, 7 Drawing Sheets

(56) References Cited

OTHER PUBLICATIONS

Guoqi Zhang et al., "Mild and Homogenous Cobalt-Catalyzed Hydrogenation of C=C, C=O, and C=N Bonds", Angewandte Chemie International Edition, (Oct. 2012), vol. 51, pp. 12102-12106.
Shaomin Fu et al., "Ligand-Controlled Cobalt-Catalyzed Transfer Hydrogenation of Alkynes: Stereodivergent Synthesis of Z- and E-Alkenes", Journal of the American Chemical Society, (Jun. 2016), vol. 138, pp. 8588-8594.
Vinod G. Landge et al., "Phosphine-free cobalt pincer complex catalyzed Z-selective semi-Hydrogenation of unbiased alkynes", Catalysis Science & Technology, (Dec. 2017), vol. 8, pp. 428-433.
Vinod G. Landge et al., "Supporting Information Phospine-free cobalt pincer complex Catalyzed Z-selective semi-hydrogenation of unbiased alkynes", Catalysis Science & Technology, (Jan. 2018), pp. S1-S48.

\* cited by examiner

COBALT COMPLEXES, PROCESS FOR PREPARATION AND USE THEREOF

FIELD OF THE INVENTION

The present invention relates to a cobalt compound of formula (I), a process for preparation and use thereof. The present invention further relates to a pharmaceutical composition and a method for inhibition of Tau Aggregation in a subject in need thereof using compound of formula (I).

BACKGROUND AND PRIOR ART OF THE INVENTION

Catalytic hydrogenation of unsaturated compounds is a fundamental synthetic transformation and has widespread applications in biorenewable, and commodity chemical production as well as in pharmaceuticals. Thus, a stereoselective semi-hydrogenation of alkynes under mild conditions is challenging and demanding. Various precious metal based homogeneous and heterogeneous catalysts were developed for semi-hydrogenation of alkynes and often promoted by a base. However, a base-free approach for catalytic hydrogenation is highly demanding, due to functional group compatibilities. Recently, Beller and coworkers reported the N-graphitic-modified cobalt nanoparticles (Co/phen@$SiO_2$-800) catalyzed semihydrogenation of alkynes to Z-alkenes under hydrogen pressure (30 bar).

Abnormal protein deposits in the brain, such as extracellular amyloid plaques and intracellular neurofibrillary tangles (NFTs), characterize Alzheimer's disease. The microtubule-associated protein Tau (MAPT) plays a key role in several neurodegenerative diseases, like Alzheimer's disease. The microtubule-associated protein Tau is expressed in the adult human brain in six different isoforms. Due to alternative splicing, two N-terminal inserts and the second out of four repeats (R2) in the C-terminal microtubule-binding domain can be present or absent (FIG. 1A). Neurofibrillary tangles consist of straight or paired helical filaments (PHFs) that are made of Tau in its hyperphosphorylated state. However, upon phosphorylation, Tau can detach from microtubules and self-assemble into amyloid fibrils. The distribution of Tau filaments correlates well with the loss of neurons and cognitive functions in AD. Tau protein is ameliorated such that it loses its affinity for MT and instead associates with itself and forms aggregates in the somatodendritic compartment. Tau is necessary for neurite outgrowth and maintenance, and suppression of Tau synthesis causes retraction and decay of neuritis.

Article titled "Mild and homogeneous Cobalt-catalyzed hydrogenation of C=C, C=O, and C=N bonds" by Guoqi Zhang et al. published in Angewandte Communications, 2012, 51, 12102-12106 reports cobalt(II) complexes of the tridentate ligand bis[2-(dicyclohexylphosphino)ethyl]amine (PNHP$^{Cy}$).

Article titled "Ligand-controlled Cobalt-catalyzed transfer hydrogenation of alkynes: Stereodivergent synthesis of Z- and E-Alkenes" by Shaomin Fu et al. published in Journal of American Chemical Society, 2016, 138 (27), pp 8588-8594 reports a novel cobalt-catalyzed stereodivergent transfer hydrogenation of alkynes to Z- and E-alkenes. Effective selectivity control is achieved based on a rational catalyst design.

Recently, methylene blue and methylthionine hydrochloride have been identified as a Tau aggregation inhibitor and reached a phase III clinical trials. Indeed, there is an urgent need for the discovery of new potential therapeutics. Therefore, there is an immense interest to identify a potential small molecule (metal complexes, natural products, and short-range peptides) for Tau aggregation inhibition or to disaggregate the paired helical filaments (PHFs) of Tau.

Therefore it is the need to develop novel catalysts for the selective hydrogenation of alkenes or alkynes at ambient temperature, phosphine-free, and neutral conditions without using any additives.

OBJECTIVES OF THE INVENTION

The main objective of the present invention is to provide a cobalt compound of formula (I) for selective hydrogenation and inhibition of Tau aggregation and a process for preparation thereof.

Another objective of the present invention is to provide a process for the selective hydrogenation of alkene or alkynes in the presence of the cobalt compound of formula (I) at ambient temperature, phosphine-free, and neutral conditions without using any additives.

Still another objective of the present invention is to provide a pharmaceutical composition comprising a compound of formula (I), or a stereoisomer, or ester or pharmaceutically acceptable salt thereof and a pharmaceutically acceptable carrier, diluent or excipient.

Yet another objective of the present invention is to provide a method for inhibition of Tau Aggregation in a subject in need thereof; comprising administering to the subject a therapeutically effective amount of the compound of formula (I) or a pharmaceutically acceptable salt thereof.

SUMMARY OF THE INVENTION

Accordingly, the present invention provides a cobalt compound of formula (I) for selective hydrogenation and inhibition of Tau aggregation and a process for the preparation thereof. In an aspect, the present invention provides a cobalt compound of formula (I) for selective hydrogenation and inhibition of Tau aggregation.

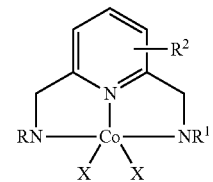

I

Wherein, X is selected from the group consisting of halides (Chloro and Bromo); pseudohalides; anionic ligands selected from CN$^-$, H$^-$, RS$^-$, RO$^-$;

R=R$^1$ or R≠R$^1$ and Both R and R$^1$ are same or different, straight or branched and represents independently of each other hydrogen, or (un)substituted or substituted alkyl, alkenyl or alkynyl; or (un)substituted or substituted aryl, heteroalkyl, heteroaryl, aiylalkyl, heteroarylalkyl; (un) substituted or substituted cycloalkyls, cycloalkenyl or cycloalkynyl; azo, amino, halo, nitro, cyano, hydroxyl, carbonyl, thiocarbonyl, carboxylic, ester, alkoxy, alkylamino, arylaminocarbamide, carbamate, hydrazine, sulfonyl, sulphide, thioether, sulphonamide, phosphates R$^2$ represents hydrogen, or (un)substituted or substituted alkyl, alkenyl or alkynyl; or (un)substituted or substituted aryl, heteroalkyl, heteroaryl, arylalkyl, heteroarylalkyl; (un) substituted or substituted cycloalkyls, cycloalkenyl or cycloalkynyl; azo, amino, halo, nitro, cyano, hydroxyl, carbonyl, thiocarbonyl, carboxylic, ester, alkoxy, alkylamino, arylaminocarbamide, carbamate, hydrazine, sulfonyl, sulphide, thioether, sulphonamide, phosphates.

In another aspect, the present invention provides a process for the synthesis of compounds of formula (I) comprising the steps of:
a) Adding a solution of 2,6-bis(bromomethyl)pyridine in acetonitrile to a solution of amine and base in solvent followed by stirring at the temperature range of 80 to 90° C. for the time period 14 to 16 hours to afford NNN-Ligand;
b) Adding a solution of Cobalt halo hexahydrate in solvent to a solution of NNN-Ligand of step (a) in solvent with stirring for 3 to 4 hours at the temperature range of 25 to 30° C. to afford the desired product of formula (I).

In still another aspect, a pharmaceutical composition comprising a compound of formula (I), or a stereoisomer, or ester or pharmaceutically acceptable salt thereof and a pharmaceutically acceptable carrier, diluent or excipient.

In yet another aspect, the present invention provides a method for Inhibition of Tau Aggregation in a subject in need thereof; comprising administering to the subject a therapeutically effective amount of the compound of formula (I) or a pharmaceutically acceptable salt thereof.

In still yet another aspect, the present invention provides a process for the selective hydrogenation of alkenes or alkynes in the presence of cobalt compound of formula (I) as a catalysts comprises mixing alkyne/alkene, amino-borane, Cobalt complex and methanol followed by stirring for the period in the range of 10-14 h at the temperature range of 50-80° C. to obtain the desired alkene/alkane.

DETAILED DESCRIPTION OF THE INVENTION

Figure 1:
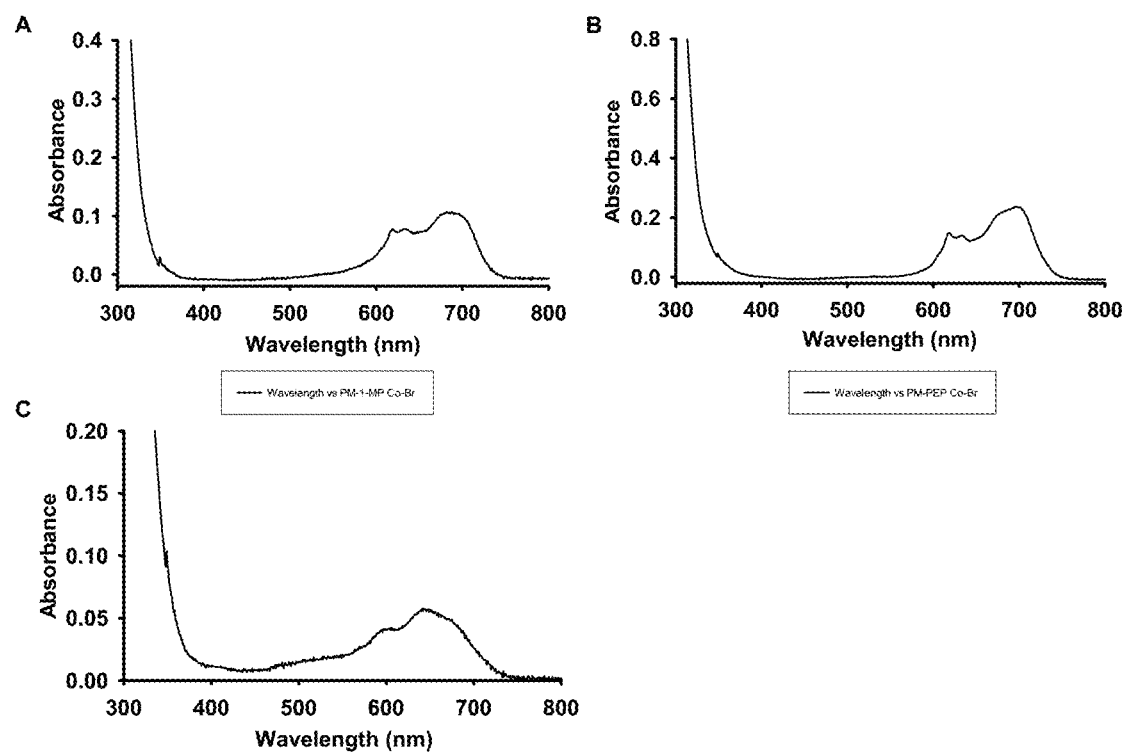
FIG. 1: UV-Vis spectra of (NNN-L1)CoCl$_2$, (NNN-L2) CoCl$_2$, and (NNN-L3)CoCl$_2$.

The invention will now be described in detail in connection with certain preferred and optional embodiments, so that various aspects thereof may be more fully understood and appreciated.

In an embodiment, the present invention provides a cobalt complex compound represented by the general formula (I),

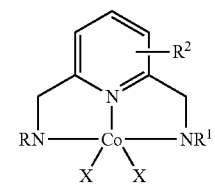

I

Wherein, X is selected from the group consisting of halides (Chloro and Bromo); pseudohalides; anionic ligands selected from CN$^-$, H$^-$, RS$^-$, RO$^-$;

R=R$^1$ or R≠R$^1$ and Both R and R$^1$ are same or different, straight or branched and represents independently of each other hydrogen, or (un)substituted or substituted alkyl, alkenyl or alkynyl; or (un)substituted or substituted aryl, heteroalkyl, heteroaryl, arylalkyl, heteroarylalkyl; (un) substituted or substituted cycloalkyls, cycloalkenyl or cycloalkynyl; azo, amino, halo, nitro, cyano, hydroxyl, carbonyl, thiocarbonyl, carboxylic, ester, alkoxy, alkylamino, arylaminocarbamide, carbamate, hydrazine, sulfonyl, sulphide, thioether, sulphonamide; phosphates R$^2$ represents hydrogen, or (un)substituted or substituted alkyl, alkenyl or alkynyl; or (un)substituted or substituted aryl, heteroalkyl, heteroaryl, arylalkyl, heteroarylalkyl; (un) substituted or substituted cycloalkyls, cycloalkenyl or cycloalkynyl; azo, amino, halo, nitro, cyano, hydroxyl, carbonyl, thiocarbonyl, carboxylic, ester, alkoxy, alkylamino, arylaminocarbamide, carbamate, hydrazine, sulfonyl, sulphide, thioether, sulphonamide, phosphates.

In a preferred embodiment, the compound of formula (I) is selected from

Cobalt(II)(2,6-bis((4-methylpiperazin-1-yl)methyl)pyridine)chloride (1A), Cobalt(II)(2,6-bis(piperazin-1-ylmethyl)pyridine)chloride (1B), Cobalt(II)(2,6-bis(morpholinomethyl)pyridine)chloride (1C), Cobalt(II)(2,6-bis(piperidin-1-ylmethyl)pyridine)chloride (1D), Cobalt(II)(2,6-bis((4-methylpiperazin-1-yl)methyl)pyridine)bromide (2A), Cobalt(II)(2,6-bis(piperazin-1-ylmethyl)pyridine) bromide (2B), Cobalt(II)(2,6-bis(morpholinomethyl)pyridine)bromide (2C), Cobalt(II)(2,6-bis(piperidin-1-ylmethyl) pyridine)bromide (2D)

1A
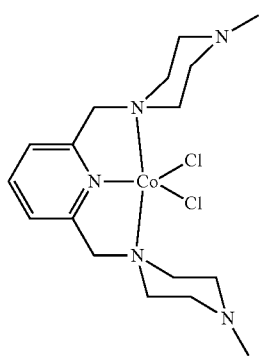
NNN-L1CoCl₂
1B
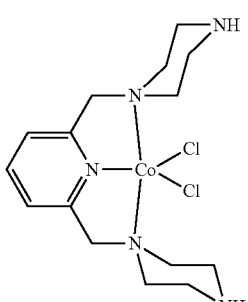
NNN-L2CoCl₂
1C
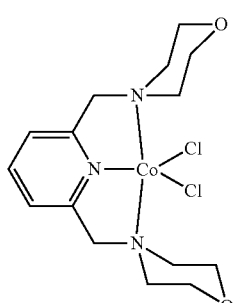
NNN-L3CoCl₂
1D
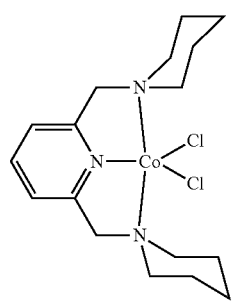
NNN-L4CoCl₂
2A
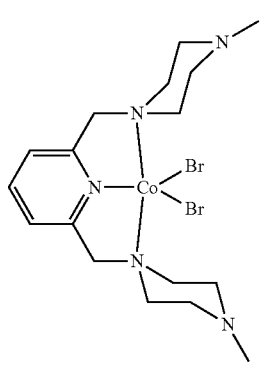
NNN-L1CoBr₂
2B
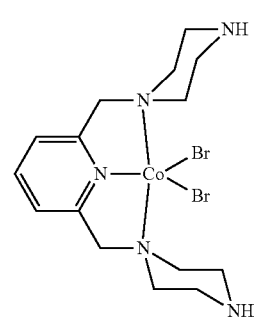
NNN-L2CoBr₂
2C
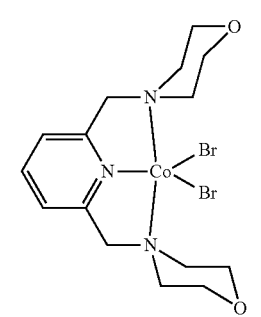
NNN-L3CoBr₂
2D
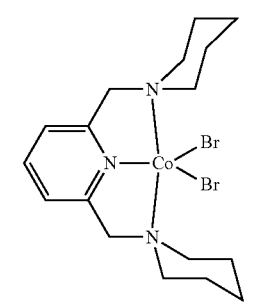
NNN-L4CoBr₂
In another embodiment; the present invention provides a process for the synthesis of compounds of formula (I) comprising the steps of:
a) Adding a solution of 2,6-bis(bromomethyl)pyridine in acetonitrile to a solution of amine and base in solvent followed by stirring at the temperature range of 80 to 90° C. for the time period 14 to 16 hours to afford NNN-Ligand;

b) Adding a solution of Cobalt halo hexahydrate in solvent to a solution of NNN-Ligand of step (a) in solvent with stirring for 3 to 4 hours at the temp range of 25 to 30° C. to afford the desired product of formula (I).

The base is selected from inorganic bases such as potassium carbonate ($K_2CO_3$), sodium carbonate ($Na_2CO_3$), lithium carbonate ($Li_2CO_3$), cesium carbonate ($Cs_2CO_3$), sodium hydride (NaH), cesium fluoride (CsF), tripotasium phosphate ($K_3PO_4$), monopotassium phosphate ($KH_2PO_4$) or potassium bicarbonate ($KHCO_3$)

The amine is selected from morpholine, piperidine or 1-methylpiperazine and any secondary and primary amines (with chiral and achiral version).

The solvent is selected from methanol, acetonitrile, ethanol, dimethylformamide (DMF), dimethyl sulfoxide (DMSO), isopropyl alcohol, tetrahydrofuran (THF) or t-amyl alcohol.

The above process is as shown below in Scheme 1 and Scheme 2:

Scheme 1. Synthesis of cobalt complexes

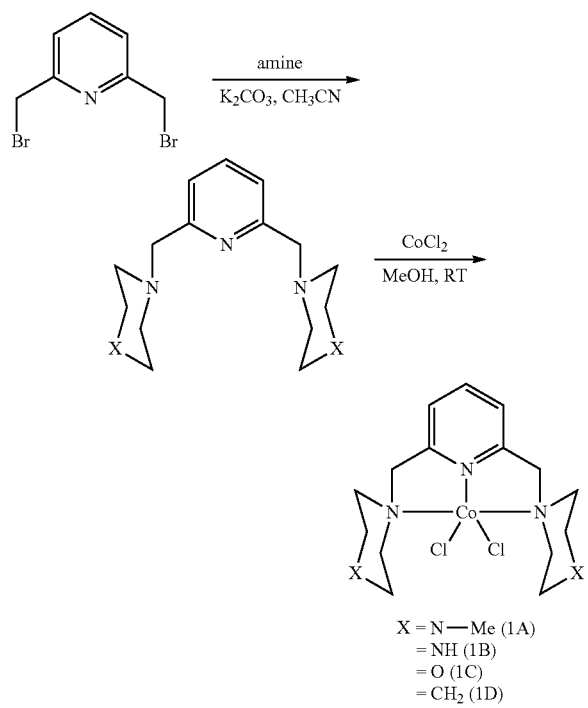

Scheme 2. Synthesis of cobalt complexes (1A-1D and 2A-2D)

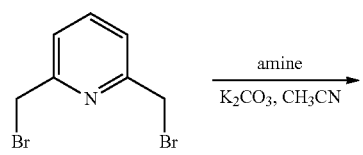

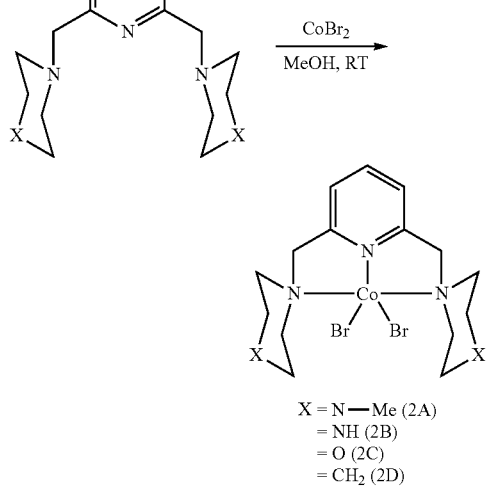

In still another embodiment, the present invention provides a pharmaceutical composition comprising a compound of formula (I), or a stereoisomer, or ester or pharmaceutically acceptable salt thereof and a pharmaceutically acceptable carrier, diluent or excipient.

In yet another embodiment, the present invention provides a method for Inhibition of Tau Aggregation in a subject in need thereof; comprising administering to the subject a therapeutically effective amount of the compound of formula (I) or a pharmaceutically acceptable salt thereof.

In still yet another aspect, the present invention provides a process for the selective hydrogenation of alkenes or alkynes in the presence of cobalt compound of formula (I) as a catalysts comprises mixing alkyne/alkene, amino-borane, Cobalt complex and methanol followed by stirring for 10-14 h at the temperature range of 50-80° C. to obtain the desired alkene/alkane.

The alkyne is selected from internal alkyne or terminal alkyne and the alkene is selected from terminal alkene.

The alkene is selected from diaryl acetylene, dialkyl acetylene preferably diphenyl acetylene and the alkene is selected from cis-stilbene derivatives.

The cobalt complex is selected from Cobalt(II)(2,6-bis((4-methylpiperazin-1-yl)methyl)pyridine)chloride (1A), Cobalt(II)(2,6-bis(piperazin-1-ylmethyl)pyridine)chloride (1B), Cobalt(II)(2,6-bis(morpholinomethyl)pyridine)chloride (1C), Cobalt(II)(2,6-bis(piperidin-1-ylmethyl)pyridine) chloride (1D), Cobalt(II)(2,6-bis((4-methylpiperazin-1-yl)methyl)pyridine)bromide (2A), Cobalt(II)(2,6-bis (piperazin-1-ylmethyl)pyridine) bromide (2B), Cobalt(II)(2, 6-bis(morpholinomethy)pyridine)bromide (2C) or Cobalt (II)(2,6-bis(piperidin-1-ylmethy)pyridine)bromide (2D).

Figure 2:
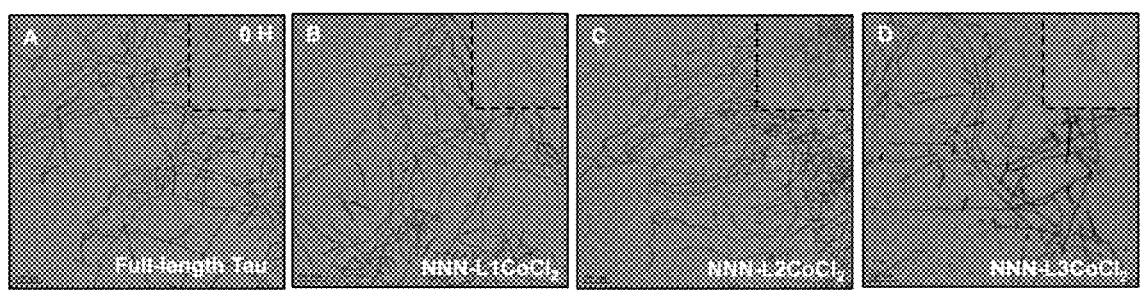
FIG. 2: The morphology of aggregates in presence of CBMCs.

FIG. 2 shows the morphology of aggregates in presence of CBMCs. A, B, C, D. The ability of Tau disaggregation by L1 (1B), L2 (1C), and L3 (1A) at 0 hour is studied by TEM analysis, where CBMCs have very negligible effect at 0 hour.

Figure 3:
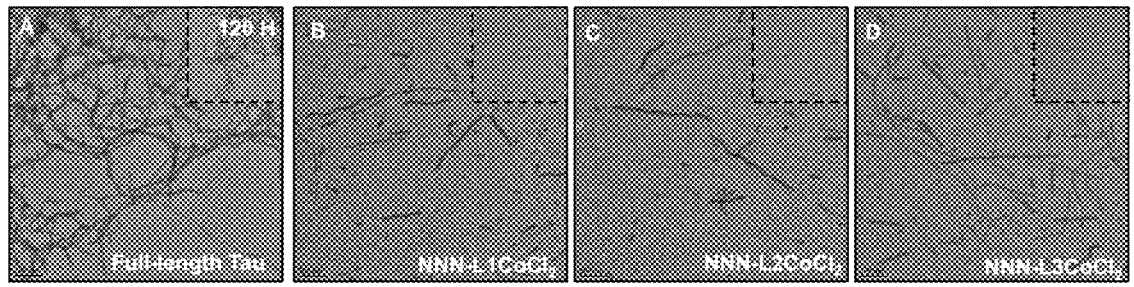
FIG. 3: Disaggregation of Tau PHFs by CBMCs.

FIG. 3 shows Disaggregation of Tau PHFs by CBMCs. A, B, C, D. Upon prolonged incubation with by L1 (1B), L2 (1C), and L3 (1A) the aggregates are destructed into shorter filaments.

Figure 4:
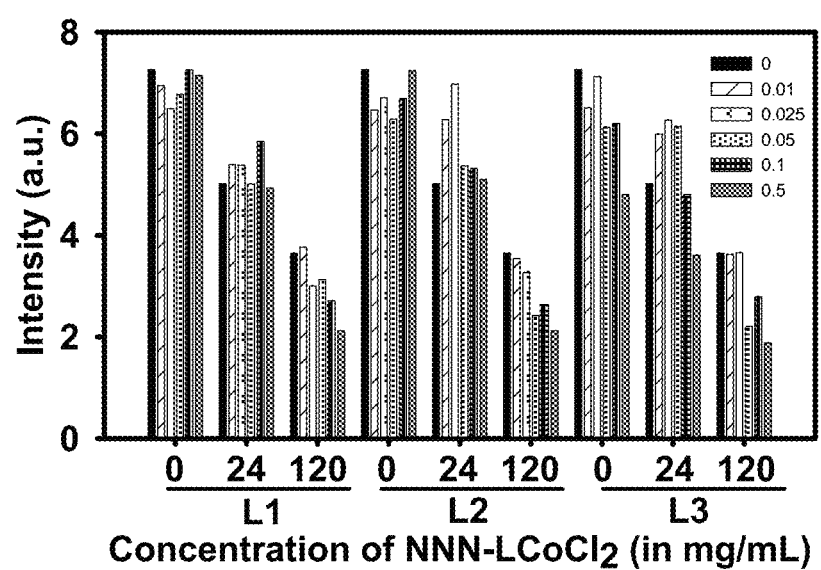
FIG. 4: The quantification of Tau disaggregation by L1, L2 and L3 respectively.

FIG. 4 shows the quantification of Tau disaggregation by L1 (1B), L2 (1C), and L3 (1A) respectively, represented as bar diagram.

Figure 5:
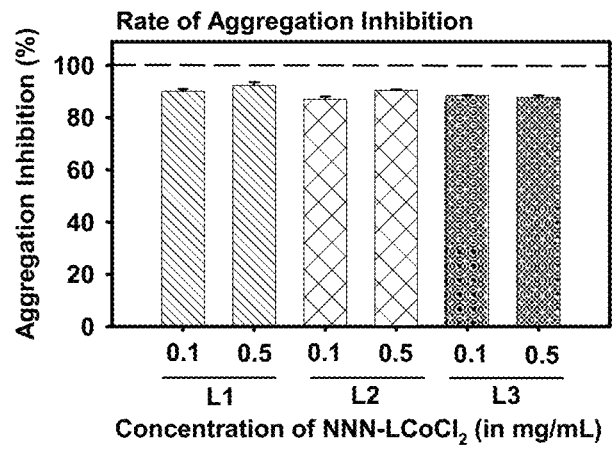
FIG. 5: Inhibition of aggregates formation by repeat Tau.

FIG. 5 shows inhibition of aggregates formation by repeat Tau. A. The polymerization of Tau is studied by using ThS to monitor the aggregates formation in presence and absence of CBMC compounds at the concentrations of 0.1 mg/mL and 0.5 mg/mL; CBMC compound is effective in inhibiting aggregates formation by repeat Tau. The intensity of fluorescence in presence of CBMC compounds is several folds lesser when compared to repeat Tau alone, indicating the ability of the compound in preventing aggregates formation. D. The bar diagram clearly depicts that the rate of aggregation inhibition by CBMC compounds are almost 90%.

Figure 6:
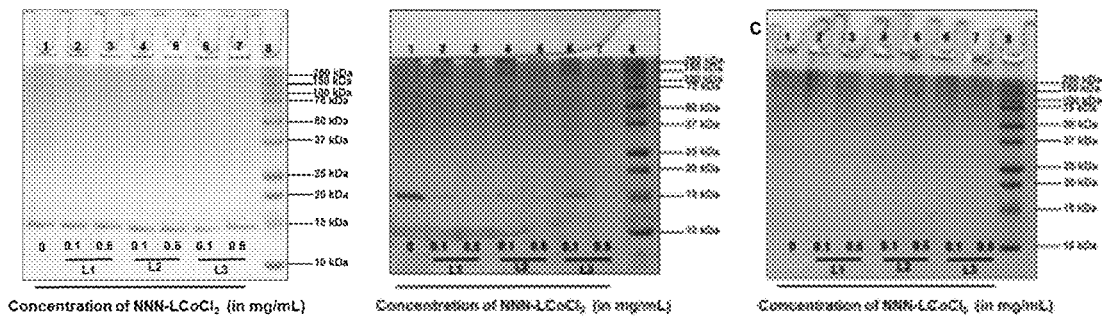
FIG. 6: Resolving Tau by SDS-PAGE to monitor higher order species.

FIG. 6 shows resolving Tau by SDS-PAGE to monitor higher order species. A, B, C. The aggregates are further analyzed by SDS-PAGE and the metal-based complex is completely inhibits the Tau aggregation in dose-dependent manner. The early hour of incubation with compounds suggest that there is minimal inhibition.

Figure 7:
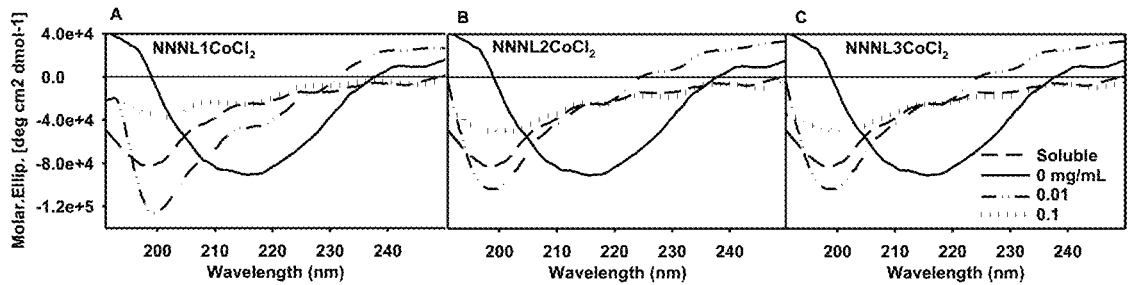
FIG. 7: Cobalt-based metal complexes induce Tau into random coil structure in solution.

FIG. 7 shows Cobalt-based metal complexes induces Tau into random coil structure in solution. A, B, C. In presence of heparin Tau aggregates to form β-sheet conformation, which is observed as a dip in the negative axis in far UV region, around 220 nm. In presence of CBMCs the random coil conformation of Tau is persistent (short dash line).

Figure 8:
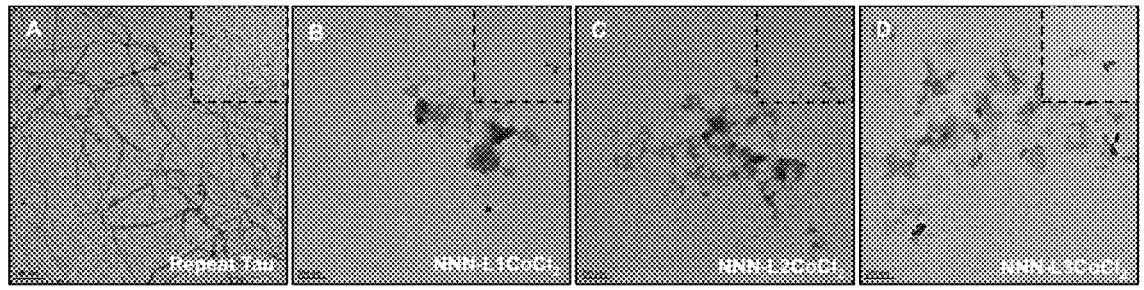
FIG. 8: CBMCs leads to amorphous aggregates formation.

FIG. 8 shows CBMCs leads to amorphous aggregates formation. A. The repeat Tau aggregates to form long filamentous morphology as observed under TEM, which is completely restricted by CBMCs. B, C, D; In presence of CBMCs the aggregates are completely amorphous in structure.

Figure 9:
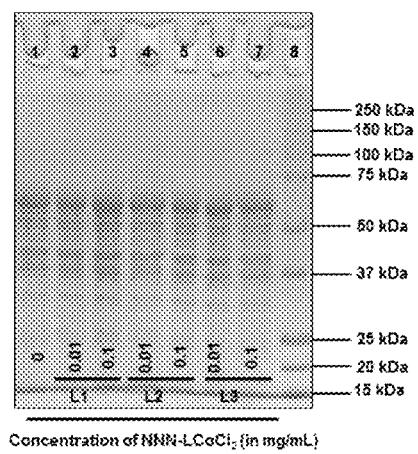
FIG. 9: Effect of CBMCs on soluble Tau analyzed by SDS-PAGE.

FIG. 9 shows effect of CBMCs on soluble Tau analysed by SDS-PAGE. A. The soluble full-length Tau is analyzed for the formation of higher order aggregates by SDS-PAGE, which revealed no aggregates formation.

Figure 10:
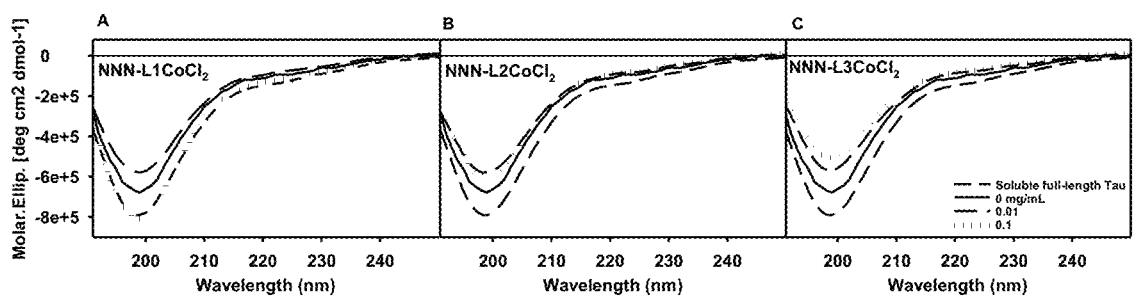
FIG. 10: Changes in soluble Tau conformation in presence of CBMCs.

FIG. 10 shows changes in soluble Tau conformation in presence of CBMCs. A, B, C. Soluble Tau in presence of metal complex do not show any conformational changes, which indicates that CBMCs are not driving the β-sheet conformation.

Figure 11:
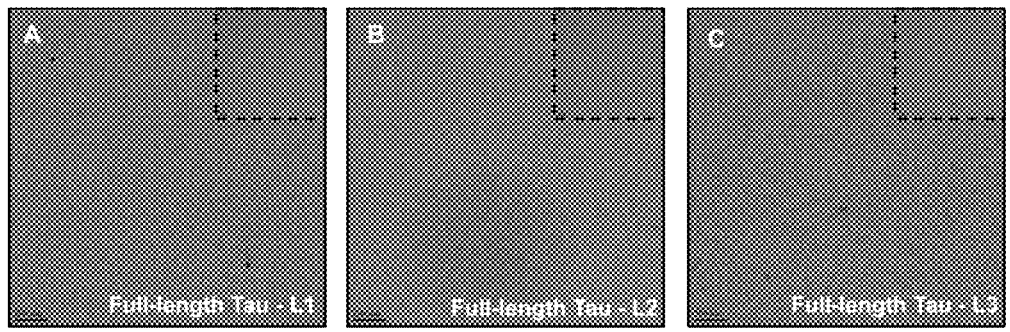
FIG. 11: TEM analysis to monitor the formation of higher order aggregates by soluble full-length Tau.

FIG. 11 shows TEM analysis to monitor the formation of higher order aggregates by soluble full-length Tau. A, B, C. Soluble full-length Tau is analyzed under TEM in presence of L1, L2 and L3 respectively, to observe the morphology of Tau aggregates formed after 1 hour incubation at 37° C.

Figure 12:
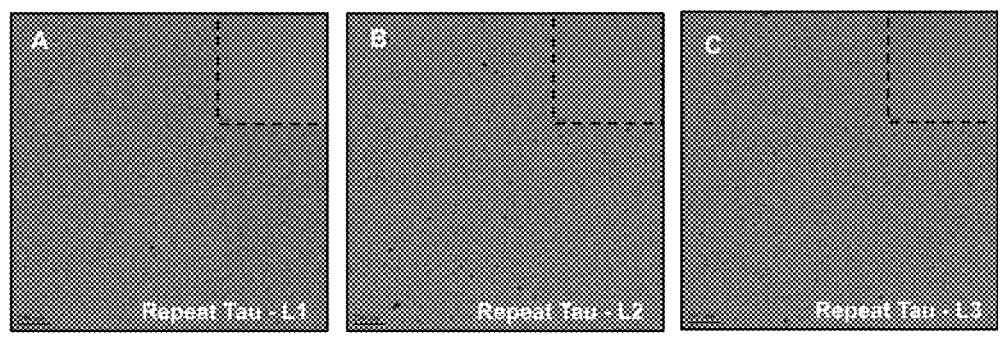
FIG. 12: Higher order aggregates formed by repeat Tau.

FIG. 12 shows higher order aggregates formed by repeat Tau. A, B, C. Four repeat Tau is observed for the formation of aggregates in presence of L1, L2 and L3 after 1 hour incubation at 37° C.

Figure 13:
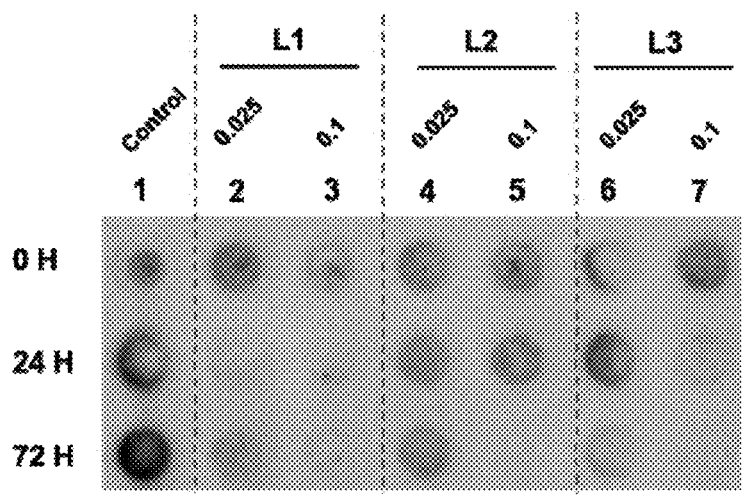
FIG. 13: Analysis of higher order species by filter trap assay.

FIG. 13 shows analysis of higher order species by filter trap assay. The effect of CBMCs in diminishing the higher order species is probed by antibodies against Tau.

Figure 14:
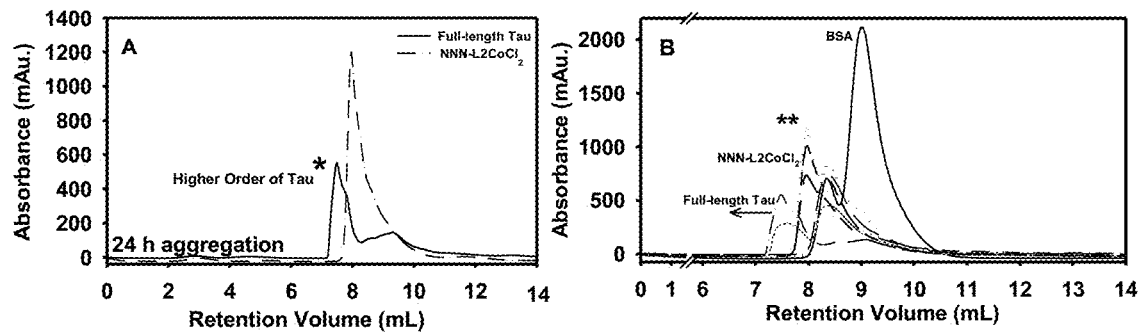
FIG. 14: CBMCs prevent the polymerization of Tau to form PHFs.

FIG. 14 shows CBMCs prevent the polymerization of Tau to form PHFs. A. The SEC analysis to detect the formation of HMW species by Tau in presence and absence of CBMCs. B. Comparing the change in retention volume of Tau protein in presence and absence of NNN-L2CoCl$_2$ at different time intervals. The retention volume of soluble Tau overlay with the known marker i.e. BSA, along with full-length diluted in assembly buffer in presence and absence of NNN-L2CoCl$_2$.

Figure 15:
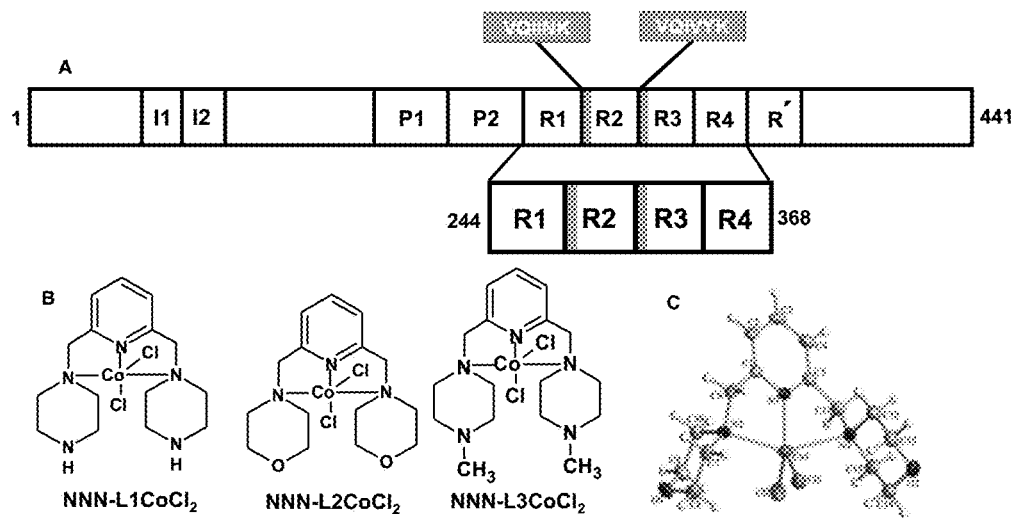
FIG. 15: A. Domain organization of full-length Tau and its four repeat Tau; B. Chemical structure of cobalt-based metal complexes; C. X-ray crystal-structure analysis of NNN-L2 CoCl$_2$

FIG. 15: A. Domain organization of full-length Tau and its four repeat Tau. The longest isoform of Tau is composed of 441 amino acids, with four repeats towards C-terminal that is crucial in both physiological as well as in AD pathology. In physiological conditions, it interacts with the tubulin dimer and helps in the assembly of MTs, while in the pathological condition they act as main nucleating centres and form the core of aggregates. The four repeat Tau comprises 120 amino acids, from 244 to 368, and has a tendency to aggregate more spontaneously when compared to full-length Tau. It consist of hexapeptides at the beginning of the second and the third repeat which are the signature motifs that are responsible for aggregation; B. Chemical structure of cobalt-based metal complexes. C. X-ray crystal-structure analysis of NNN-L2CoCl$_2$ with 50% probability of thermal ellipsoids; Selected bond length[A°] and angle[°]: Co(1)-N(1) 2.0265, Co(1)-N(2) 2.3215, Co(1)-N(3) 2.4530, N(1)-Co(1)-N(2) 76.97, N(1)-Co(1)-N(3) 73.51, Cl1(1)-Co(1)-Cl1(2) 113.56.

Figure 16:
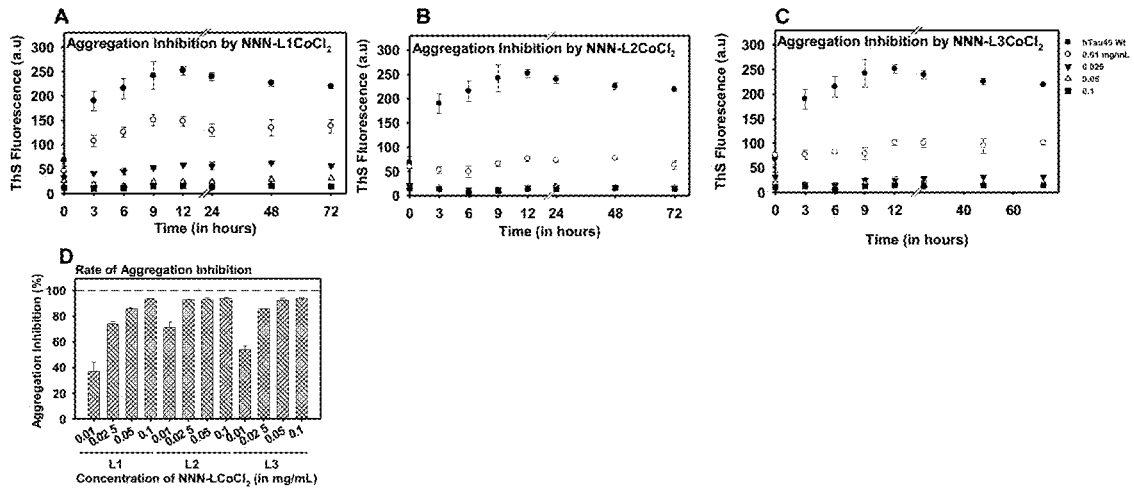
FIG. 16: Cobalt-based complex inhibits Tau aggregation.

FIG. 16: Cobalt-based complex inhibits Tau aggregation. A, B, C. The aggregation inhibition of full-length Tau in presence of CBMCs monitored by ThS fluorescence. The aggregation is induced from full-length Tau in presence of heparin as inducer and assembly buffer. The typical full-length Tau reaches its highest propensity of aggregation, but the incorporation of cobalt complex completely decreases its aggregation rate with increasing concentration of metal complex. D. Although all three complexes are compelling in inhibiting aggregation process, the lower concentration of L2 is more effective in comparison with L1 and L3. At higher concentrations of 0.05 and 0.1 mg/mL L2, and L3 show maximum inhibition of about 97%. L1 at its highest concentration of 0.1 mg/mL also has an inhibition rate of 97%, which clearly suggests the proficiency of these metal complexes in inhibiting Tau aggregation.

Figure 17:
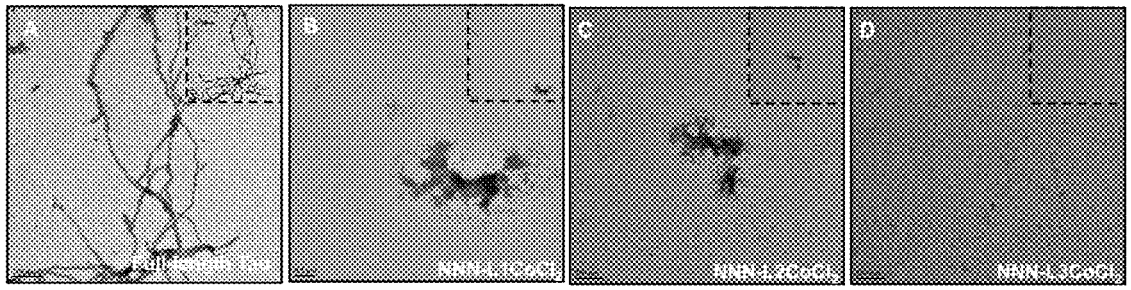
FIG. 17: Conformation of full-length Tau measured by CD spectroscopy.

FIG. 17: Full-length Tau fibrils mapped by TEM; A, B, C, D. The morphology of Tau upon incubation with inducer alone and the typical morphology of Tau fibrils are observed. In presence of CBMCs stipulated their ability to prevent aggregates formation.

Figure 18:
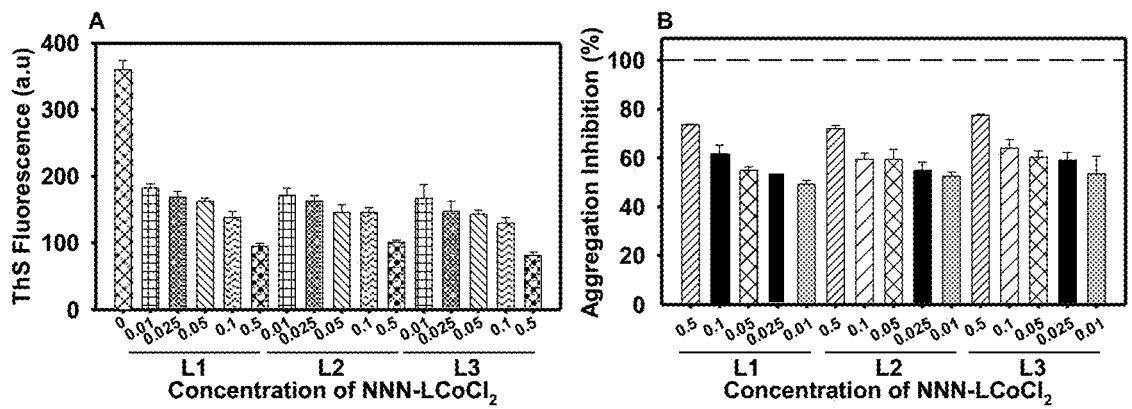
FIG. 18: Disaggregation of full-length Tau.

FIG. 18: Disaggregation of full-length Tau: A. The effect of disaggregation by L1, L2, and L3 conjugated to CoCl$_2$ is analysed by ThS fluorescence assay. Tau aggregates is incubated with CBMCs in an increasing concentration of 0.01 mg/mL to 0.1 mg/mL; B. It is observed that the highest concentration of L3shows 77% reduction in disaggregation, whereas L1 and L2 showed 74 and 72% disaggregation respectively.

Following examples are given by way of illustration therefore should not be construed to limit the scope of the invention.

EXAMPLES

Example 1: 2,6-bis(morpholinomethyl)pyridine

A solution of 2,6-bis(bromomethyl)pyridine (0.3 g, 1.13 mmol) in acetonitrile (30 mL) was added dropwise to solution of morpholine (0.197 g, 2.26 mmol) and K$_2$CO$_3$ (0.468 g, 3.39 mmol) in CH$_3$CN (15 mL), the resulting reaction mixture was allowed to stir for 14 h at 80° C., then cooled to 25° C., subsequently the reaction mixture was extracted with chloroform. The organic layer was collected and dried over anhyd.Na$_2$SO$_4$, then evaporated in vacuum under the reduced pressure afforded NNN-L1. Yield (0.282 g, 90%). IR (KBr): ν=2800 (m), 1575 (m), 1454 (m), 1298 (m), 1111 (s), 906 (m). $^1$H NMR (500 MHz, CHLOROFORM-d) δ=7.65-7.52 (m, 1H), 7.31 (d, J=7.6 Hz, 2H), 3.84-3.69 (m, 8H), 3.66 (s, 4H), 2.51 (s, 8H). $^{13}$C NMR (126 MHz, CHLOROFORM-d) δ=157.7, 136.7, 121.4, 77.3, 76.7, 66.9, 64.8, 53.7. HRMS (ED: m/z Calcd for C$_{15}$H$_{24}$O$_2$N$_3$: 278.1869; Found: 278.1863.

Example 2: 2,6-bis(piperidin-1-ylmethyl)pyridine

A solution of 2,6-bis(bromomethyl)pyridine (152 mg, 0.55 mmol) in acetonitrile (5 mL) was added dropwise to solution of piperidine (1.1 mmol) and $K_2CO_3$ (331 mg, 2.42 mmol) in $CH_3CN$ (10 mL), the resulting reaction mixture was allowed to stir for 14 h at 80° C., then cooled to 25° C., subsequently the reaction mixture was extracted with chloroform. The organic layer was collected and dried over anhyd. $Na_2SO_4$, then evaporated in vacuum under the reduced pressure afforded NNN-L2. Yield (131 mg, 88%). $^1H$ NMR (500 MHz, CHLOROFORM-d) δ=7.70-7.54 (m, 1 H), 7.30 (d, J=7.6 Hz, 2 H), 3.62 (s, 4 H), 2.44 (br. s., 8 H), 1.65-1.55 (m, 8 H), 1.50-1.41 (m, 4 H). $^{13}C$ NMR (126 MHz, CHLOROFORM-d) δ=158.4, 136.4, 121.0, 77.3, 76.7, 65.3, 54.7, 25.9, 24.2. HRMS (EI): m/z Calcd for $C_{17}H_{28}N_3$: 274.2283; Found: 274.2278.

Example 3:
2,6-bis((4-methylpiperazin-1-yl)methyl)pyridine

A solution of 2,6-bis(bromomethyl)pyridine (0.8 g, 3.0 mmol) in acetonitrile (45 mL) was added dropwise to solution of 1-methylpiperazine (0.669 g, 6.0 mmol) and $K_2CO_3$ (1.249 g, 9.0 mmol) in CH3CN (20 mL), the resulting reaction mixture was allowed to stir for 14 h at 80° C., then cooled to 25° C., subsequently the reaction mixture was extracted with chloroform. The organic layer was collected and dried over anhyd.$Na_2SO_4$then evaporated in vacuum under the reduced pressure afforded NNN-L3. Yield (0.82 g; 89%). IR (κBr): ν=2945 (s), 2520 (m), 2042 (m), 1452 (s), 1029 (s), 651 (m). $^1H$ NMR (500 MHz, CHLOROFORM-d) δ=7.59 (s, 1H), 7.28 (s, 2H), 3.66 (s, 4H), 2.54 (s, 8H), 2.46 (s, 8H), 2.28 (s, 6 H). $^{13}C$ NMR (126 MHz, CHLOROFORM-d) δ=158.0, 136.6, 121.3, 77.3, 76.7, 64.4, 55.1, 53.2, 46.1. HRMS (ED: m/z Calcd for $C_{17}H_{30}N_5$: 304.2501; Found: 304.2496.

Example 4: Synthesis of (NNN-L1)$CoCl_2$

Cobalt chloride hexahydrate (0.312 g, 1.34 mmol) in methanol (15 mL) was added dropwise to solution of NNN-L1 (0.408 g, 1.34 mmol) in MeOH (15 mL) with stirring. The resulting reaction mixture was allowed to stir for 3 hours at 25° C. The resulting solution was evaporated under vacuum afforded the blue color solid; the solid was washed with diethyl ether and dried at air. Yield (0.54 g; 93%). IR (KBr): ν=2924 (s), 2314 (m), 1612 (m), 1462 (s), 1207 (m), 972 (m). HRMS (ED: m/z Calcd for $C_{17}H_{30}N_5Cl_2Co$: 433.1210; Found: 433.1205.

Example 5: Synthesis of (NNN-L2)$CoCl_2$

Cobalt chloride hexahydrate (0.086 g, 0.36 mmol) was added to solution of NNN-L1 (0.1 g, 0.36 mmol) in MeOH (10 mL) with stirring. The resulting reaction mixture was allowed to stir for 3 hours at 25° C. The resulting solution was concentrated in a vacuum afforded the blue color solid; the solid was washed with diethyl ether and dried at air. Yield (0.132 g; 90%). IR (KBr): ν=3446 (w), 1633 (s), 1460 (m), 1165 (m), 989 (m), 613 (m). HRMS (ESI): calcd. For $C_{16}H_{28}Cl_2CoN_5$ [M+Na]$^+$ 405.23; found 429.24.

Example 6: Synthesis of(NNN-L3)$CoCl_2$

Cobalt chloride hexahydrate (0.129 g, 0.54 mmol) in methanol (8 mL) was added dropwise to solution of NNN-L3 (0.151 g, 0.54 mmol) in MeOH (10 mL) with stirring. The resulting reaction mixture was allowed to stir for 3 hours at 25° C. The resulting solution was evaporated under vacuum afforded the blue colored solid and the solid was washed with diethyl ether and dried at air. Yield (0.21 g, 95%). IR (KBr): ν=2958 (s), 2841 (m), 1610 (s), 1450 (m), 1290 (m), 1111 (s), 999 (m), 869 (s), 815 (m). HRMS (EI): m/z Calcd for $C_{17}H_{28}N_3Cl_2Co$: 403.0992; Found: 403.0987.

Example 7: Synthesis of Cobalt-Complex 2A

Anhydrous $CoBr_2$ (200 mg, 1 equiv.) in methanol (5 mL) was added dropwise to solution of NNN-L1 (1 equiv) in MeOH (2 mL) with stirring. The resulting reaction mixture was allowed to stir for 3 h at 25° C. The resulting solution was evaporated under vacuum afforded the blue color solid; the solid was washed with diethyl ether and dried at air. Yield (136 mg, 82%); IR (KBr): 2962, 2844, 2360, 1611, 1575, 1454, 1441, 1358, 1287, 1112, 1001, 871, 815, 787, 636 cm$^{-1}$. HRMS (EI): m/z Calcd for $C_{15}H_{24}O_2N_3Br_2Co$: 494.9567; Found: 494.9562. The crystal suitable for a single-crystal X-ray diffraction was obtained from MeOH: diethyl ether (by diffusion method) at 25° C. after one day.

Example 8: Synthesis of Cobalt-Complex 2B

Anhydrous $CoBr_2$ (200 mg, 1 equiv.) in methanol (5 mL) was added dropwise to solution of NNN-L2 (1 equiv) in MeOH (2 mL) with stirring. The resulting reaction mixture was allowed to stir for 3 h at 25° C. The resulting solution was evaporated under vacuum afforded the blue color solid; the solid was washed with diethyl ether and dried at air. Yield (151 mg, 91%). IR (KBr): 2934, 2853, 2703, 2360, 1610, 1455, 1356, 1263, 1165, 1084, 985, 858, 769, 619 cm$^{-1}$. HRMS (EI): m/z Calcd for $C_{17}H_{28}N_3Br_2Co$: 403.9982; Found: 490.9976.

Example 9: Synthesis of Cobalt-Complex 2C

Anhydrous $CoBr_2$ (200 mg, 1 equiv.) in methanol (5 mL) was added dropwise to solution of NNN-L3 (1 equiv) in MeOH (2 mL) with stirring. The resulting reaction mixture was allowed to stir for 3 h at 25° C. The resulting solution was evaporated under vacuum afforded the blue color solid; the solid was washed with diethyl ether and dried at air. Yield (103 mg, 62%). IR (KBr): 2934, 2853, 2703, 2360, 1610, 1455, 1356, 1263, 1165, 1084, 985, 858, 769, 619 cm$^{-1}$. HRMS (EI): m/z Calcd for $C_{17}H_{28}N_3Br_2Co$: 403.9982; Found: 490.9976. Yield (131 mg, 79%). IR(KBr): 2962, 2844, 2360, 1611, 1575, 1454, 1441, 1358, 1287, 1112, 1001, 871, 815, 787, 636 cm$^{-1}$. HRMS (EI): m/z Calcd for $C_{17}H_{30}N_5Br_2Co$: 521.0194; Found: 521.0200.

Example 10: General Procedure for Z Selective Semi-Hydrogenation of Internal Alkynes

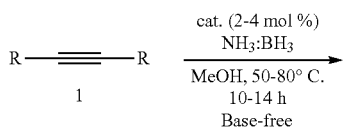

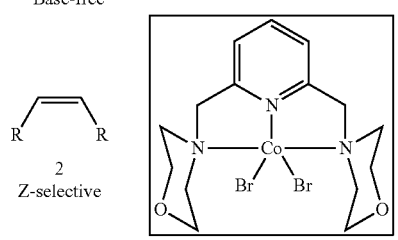

To an oven-dried 10 mL screw-capped vial, alkyne 1 (0.5 mmol), amino-borane (0.6 mmol), Co-complex (2-4 mol %) and methanol (1 mL) were added under a gentle stream of argon. The mixture was stirred for 10-14 h at 50-80° C. (bath temperature) followed by cooling to 25° C. The mixture was filtered through a celite pad with several washings (3×3 mL dichloromethane) and concentrated in vacuo. The yield of alkene was determined by GC with diphenyl as the internal standard.

TABLE 1

Scope of internal alkynes.[a]

Symmetrical alkynes

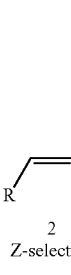
1a
94% (Z/E:100/0)

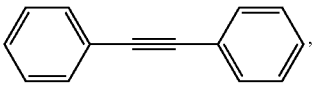
1b
52% (Z/E:100/0)[b]

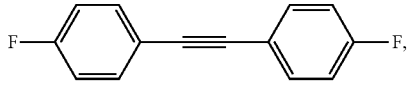
1c
76% (Z/E:100/0)[b]

Unsymmetrical alkynes

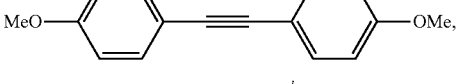
1d
88% (Z/E:100/0)

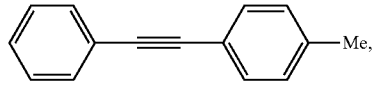
1e
70% (Z/E:90/10)

TABLE 1-continued

Scope of internal alkynes.[a]

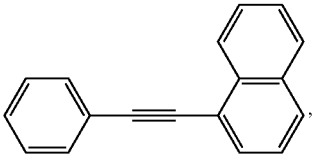

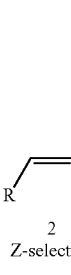
1f
93% (Z/E:100/0)[c]

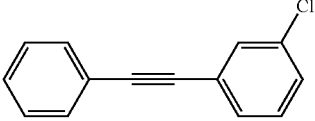
1g
73% (Z/E:100/0)[c]

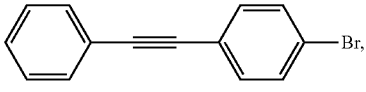
1h
36% (Z/E:100/0)

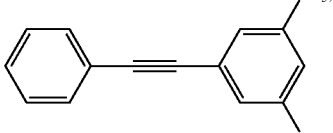
1i
34% (Z/E:100/0)[d]

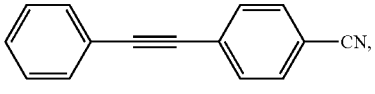
1j
82% (Z/E:100/0)

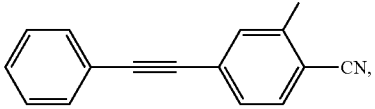
1k
33% (Z/E:100/0)[e]

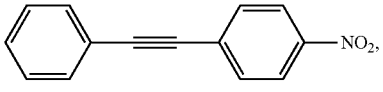
1l
90% (Z/E:100/0)[f]

TABLE 1-continued

Scope of internal alkynes.[a]

R—≡—R  1  →  cat. I (2-4 mol %), H$_3$N:BH$_3$, MeOH, 50-80° C., 10-14 h  →  (Z)-RCH=CHR  2  Z-selective cat. I: pyridine-2,6-bis(methylene) bridged bis(morpholine) Co(Br)$_2$ complex

1m Ph—C≡C—(5-methylpyridin-2-yl), 62% (Z/E:80/20)

1n Ph—C≡C—(2-thienyl), 60% (Z/E:90/10)

Acylic Polysubstituted alkynes and aliphatic alkynes

1o PhCH$_2$CH$_2$—C≡C—Me (from phenyl), 99% (Z/E:94/6)

1p Ph—C≡C—CH$_2$CH$_2$—OTBS, 91% (Z/E:100/0)[f]

1q Ph—C≡C—CH$_2$—OH, 52% (Z/E:100/0)

1r Ph—C≡C—CO$_2$Me, 80% (Z/E:84/16)[g]

1s Ph—C≡C—TMS, 23% (Z/E:70/30)

1t Me—CH$_2$—C≡C—CH$_2$—Me, 88% (Z/E:94/6)

1u PhCH(Me)—N(CH$_2$Ph)—CH$_2$—C≡C—Me, 88% (Z/E:100/0)[f]

[a]Reaction conditions: 1 (0.5 mmol), ammonia-borane (AB) (0.6 mmol), and 4.0 mol % I in 1 mL of MeOH at 80° C. for 14 h and GC yields of alkenes with Z/E ratios are shown.
[b]50° C. for 14 h.
[c]50° C. for 10 h.
[d]0.8 mmol of AB was used.
[e]AB (0.5 mmol) and 2 mol % I was used.
[f]Isolated yield.
[g]reaction time is 30 min.

Example 11: General Procedure for Semi-Hydrogenation of Terminal Alkynes

R-Ar—C≡CH  4  →  4 mol % cat, NH$_3$:BH$_3$, MeOH, 50° C., 8 h, Base free  →  R-Ar—CH=CH$_2$ To an oven-dried 10 mL screw-capped vial, terminal alkyne 4 (0.5 mmol), amino-borane (0.6 mmol), Co-complex 1A (4 mol %) and methanol (1 mL) were added under a gentle stream of argon. The mixture was stirred for 8 h at 50° C. (bath temperature) followed by cooling to 25° C. The mixture was filtered through a celite pad with several washings (3×3 mL dichloromethane) and concentrated in vacuo. The yield of alkene was determined by GC with diphenyl as the internal standard.

TABLE 2
Scope of terminal alkynes.[a]

R—C₆H₄—C≡CH → (2 mol % I, H₃N:BH₃, MeOH, 50° C., 8 h) → R—C₆H₄—CH=CH₂

4 → 5

4a: MeO—C₆H₄—C≡CH, 98%, 94%

4b: Me₂N—C₆H₄—C≡CH, 90%, 79%

4c: F—C₆H₄—C≡CH, 70%, 67%

4d: Me—C₆H₄—C≡CH, 98%, 96%

4e: 2-Cl—C₆H₄—C≡CH, 100%, 95%[b]

4f: TBSO—CH₂CH₂—C≡CH, 100%, 91%

[a] Reaction conditions: 4 (0.5 mmol), AB (0.6 mmol), and 2 mol % I in 1 mL of MeOH at 50° C. for 8 h and GC conversion of alkynes and yields of alkenes are shown.
[b] A trace amount of complete reduced product (alkane) was observed.

Example 12: General Procedure for Hydrogenation of Terminal Alkenes

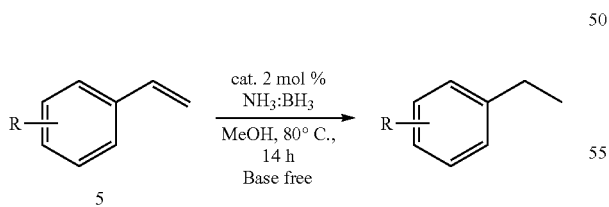

R—C₆H₄—CH=CH₂ →(cat. 2 mol % NH₃:BH₃, MeOH, 80° C., 14 h, Base free)→ R—C₆H₄—CH₂CH₃

5

To an oven-dried 10 mL screw-capped vial, alkene 5 (0.5 mmol), amino-borane (0.6 mmol), catalyst 1A (2 mol %) and methanol (1 mL) were added under a gentle stream of argon. The mixture was stirred for 14 h at 80° C. (bath temperature) followed by cooling to 25° C. The mixture was filtered through a celite pad with several washings (3×3 mL dichloromethane) and concentrated in vacuo. The yield of alkane was determined by GC with diphenyl as the internal standard.

TABLE 3
Cobalt-catalyzed hydrogenation of terminal alkenes.[a]

R—C₆H₄—CH=CH₂ → (4 mol % I, H₃N:BH₃, MeOH, 80° C., 14 h) → R—C₆H₄—CH₂CH₃

5

5a: MeO—C₆H₄—CH=CH₂, 90%, 86%

5b: F₃C—C₆H₄—CH=CH₂, 100%, 98%

5c: Cl—C₆H₄—CH=CH₂, 100%, 97%

5d: 2,4-(H₃C)₂—C₆H₃—CH=CH₂, 95%, 81%

5e: 2-Cl—C₆H₄—CH=CH₂, 85%, 78%

5f: PhS—CH₂—CH=CH₂, 23%, 17%

5g: Ph—CH₂—CH=CH₂, 100%, 98%

5h: CH₂=CH—CH(OEt)₂, 99%, 90%

5i: CH₃(CH₂)₅CH=CH₂, 100%, 70%

TABLE 3-continued

Cobalt-catalyzed hydrogenation of terminal alkenes.[a]

$$R\underset{5}{\overset{}{\bigotimes}}\xrightarrow[\substack{\text{MeOH,} \\ 80^\circ \text{ C.,} \\ 14 \text{ h}}]{\substack{4 \text{ mol \% I} \\ \text{H}_3\text{N:BH}_3}} R\overset{}{\bigotimes}$$

5j (cyclohexene) (n.r)

5k Ph—CH=CH—Me (n.r)

5l Me₂C=CH—Ph (n.r)

[a]Reaction conditions: 4 (0.5 mmol), AB (0.6 mmol), and 4 mol % I in 1 mL of MeOH at 80° C. for 14 h and GC conversion of alkenes and yields of alkanes are shown.

Example 13: Application of Cobalt-Catalyzed Strategy in Purification of Alkenes from Alkyne Impurities

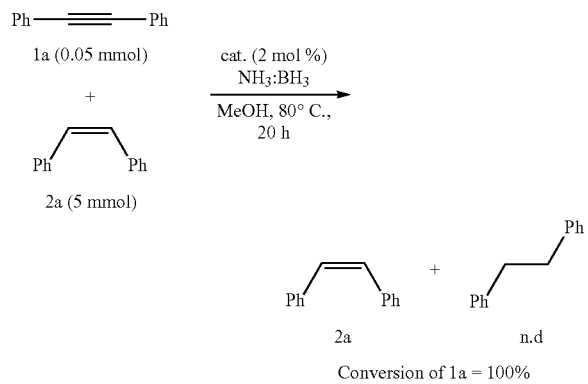

Conversion of 1a = 100%

To an oven-dried 10 mL screw-capped vial, 1a (0.05 mmol), 2a (5 mmol), amino-borane (5.1 mmol), 1A (4 mol %), and methanol (2 mL) were added under a gentle stream of argon. The mixture was stirred for 20 h at 80° C. (bath temperature) followed by cooling to 25° C. The mixture was filtered through a celite pad with several washings (3×3 mL dichloromethane) and concentrated in vacuo. The conversion alkyne and the yield of alkene were determined by GC with diphenyl as the internal standard.

Example 14: Preparation of Tau Aggregates

Tau was induced to aggregate as described previously with certain modifications. In presence heparin (17,500 Da) in the ratio of 4:1, Tau was polymerized in assembly buffer containing 20 mM BES. pH 7.4, 25 mM NaCl, 1 mM DTT, 0.01% NaN₃ and protease inhibitor cocktails. The reaction mixture was incubated at 37° C. and the aggregates formation was monitored by ThS fluorescence, SDS-PAGE and TEM at certain time intervals. The Tau protein was allowed to assemble in presence and absence of compounds in increasing concentrations with constant Tau concentrations of 0.91 mg/mL and 0.28 mg/mL for full-length and four repeat Tau respectively. The changes in the conformation of Tau protein was monitored by CD spectroscopy.

Disaggregation assay: The potency of the metal complexes for disaggregating the preformed Tau aggregates was also analysed. Soluble Tau was dissolved in assembly buffer and was incubated at 37° C. for PHF assembly. The formation of aggregates was analysed by fluorescence assay and SDS-PAGE. Thus formed aggregates were diluted to 0.91 mg/mL final concentration in 20 mM BES buffer, pH 7.4 and this mixture was incubated with increasing concentration of metal complex as discussed earlier.

Thioflavin S fluorescence assay: 5 µl of reaction mixture was diluted with 8 µM ThS in 50 mM ammonium acetate, pH 7.4 and added to 384 well plates in triplicates. Subsequently blank was also prepared for subtracting background fluorescence. The plate was incubated in the dark before measuring ThS fluorescence for 20 minutes, at an emission wavelength of 521 nm by exciting it at 440 nm in Tecan Infinite 200 PRO multimode microplate reader.

SDS-PAGE analysis for Tau aggregates: The effect of the compounds on inhibiting the aggregates formation by Tau was observed by performing SDS-PAGE. The reaction mixtures incubated with and without compound were collected at different time intervals of 0 hour, 24 hour and 60 hour (end point) and resolved on 10% SDS-PAGE using Bio-Rad electrophoresis unit. Further the gel was quantified and analysed using Gel Doc™ XR+ System and image lab software.

Soluble Tau Assay: The soluble Tau was studied in presence of metal complexes alone to analyse the conformational changes occurring due to the compound. 20 µM Tau was incubated for 1 hour at 37° C. with and without different concentrations of 0.01 mg/mL, 0.025 mg/mL, 0.05 mg/mL and 0.1 mg/mL of metal complexes. At the end of one hour the samples were analysed by SDS-PAGE, TEM and CD spectroscopy to monitor the formation of aggregates and change in Tau conformation, respectively.

CD spectroscopy: CD spectroscopy was performed in far UV region to study the conformational changes in the protein. Tau is a random coiled protein and upon aggregation it acquires β-sheet conformation. The impact of the compounds on preventing the formation of β-sheet structure was studied by CD spectroscopy. The spectrum was collected as described previously, in Jasco J-815 spectrometer, by using cuvette with 1 mm path length. The measurements were performed in the range of 250 nm to 190 nm, with a data pitch of 1.0 nm, scanning speed of 100 nm/min. All the spectra were obtained at 25° C. The reaction mixture was diluted to 3 µM in 50 mM phosphate buffer, pH 6.8. The effect of compound on soluble Tau was also studied by incubating Tau along with compounds alone at 37° C. and the spectra was read at 25° C.

Transmission Electron Microscopy (TEM): The degree of aggregates formation in presence of the metal complexes was analysed by TEM (Tecnai T-20). The assay mixture was diluted to 1 µM final concentration and spotted on the carbon coated copper grids. This was further stained by 2% uranyl acetate to observe the morphology of aggregates under TEM.

Filter trap assay: The high molecular weight (HMW) species formed by Tau in presence and absence of CBMCs were analysed. 20 µL of 20 µM Tau samples incubated with CBMCs were applied onto the nitrocellulose (NC) paper with the help of vacuum. The blot was treated with blocking buffer containing 5% skimmed milk in PBST for 1 hour. This was followed by addition of K9JA antibody in the ratio of 1:8000 dilutions prepared in blocking buffer and incubated for 1 hour, where it interacts with Tau. The blot was then subjected to three subsequent PBST washes for 10 minute each. Then secondary antibody i.e., goat anti-rabbit HRP conjugated IgG against K9JA was added and incubated for 1 hour. Further three PBST washes were given for 10 minutes each. At the end blot was washed in PBS and was carried for development by ECL reagent and the chemiluminisence signal was recorded by using Amersham Imager 600.

Size-exclusion chromatography (SEC): The HMW species formed by Tau polymerization was analysed by SEC. Tau protein was diluted to a concentration of 4.58 mg/mL in assembly buffer along with heparin in a ratio of 4:1 and incubated at 37° C. in presence and absence of 0.1 mg/mL of NNN-L2CoCl$_2$. Tau was subjected to SEC using Superdex 75 PG in order to resolve aggregated Tau from the soluble, which is accessed as decrease in retention volume at different time points of 0, 2 and 24 hours in presence and absence of NNN-L2CoCl$_2$.

ADVANTAGES OF THE INVENTION a. Novel cobalt catalysts.
b. Disclose a simple, phosphine-free process of hydrogenation carried out at neutral conditions without using any additives.
c. Compounds useful for inhibition of Tau Aggregation.
d. Compounds dissolve the pre-formed fibrils.

We claim:

1. A cobalt complex compound selected from a group consisting of Cobalt(II)(2,6-bis((4-methylpiperazin-1-yl)methyl)pyridine) chloride 1A), Cobalt(II)(2,6-bis(piperazin-1-ylmethyl)-pyridine) chloride (IB), Cobalt(II)(2,6-bis(morpholinomethy)pyridine) chloride (1C), Cobalt(II)(2,6-bis(piperidin-1-ylmethyl)pyridine) chloride (ID), Cobalt(II)(2,6-bis((4-methylpiperazin-1 yl)methyl)pyridine) bromide (2A), Cobalt(II)(2,6-bis(piperazin-1-ylmethyl)pyridine) bromide (2B), Cobalt(II)(2,6-bis(morpholinomethyl)pyridine) bromide (2C), and Cobalt(II)(2,6-bis(piperidin-1-ylmethyl)pyridine)bromide (2D).

2. A process for synthesis of cobalt complex compounds each as claimed in claim 1, comprising the steps of:
   a) adding a solution of 2,6-bis(bromomethyl)pyridine in acetonitrile to a solution of an amine and a baser in solvent followed by stirring at a temperature in the range of 80 to 90° C. for a period in the range of 14 to 16 hours to afford NNN-Ligand;
   b) adding a solution of Cobalt halo hexahydrate in solvent to a solution of NNN-Ligand of step (a) in solvent with stirring for 3 to 4 hours at a temperature range of 25 to 30° C. to afford the desired cobalt complex compounds.

3. The process as claimed in claim 2, wherein said base is selected from the group consisting of potassium carbonate, sodium carbonate, lithium carbonate, caesium carbonate, sodium hydride, cesium fluoride, tripotasium phosphate, monopotassium phosphate or potassium bicarbonate.

4. The process as claimed in claim 2, wherein said amine is selected from the group consisting of morpholine, piperidine 1-methylpiperazine, and piperazine.

5. The process as claimed in claim 2, wherein said solvent is selected from the group consisting of methanol, acetonitrile, ethanol, dimethylformamide, dimethyl sulfoxide, isopropyl alcohol or tetrahydrofuran.

6. A pharmaceutical composition comprising the compound according to claim 1, or a stereoisomer, or ester or pharmaceutically acceptable salt thereof and a pharmaceutically acceptable carrier, diluent or excipient.

7. A method for inhibiting Tau aggregation in a subject in need thereof, the method comprising administering to the subject a therapeutically effective amount of the cobalt complex compound according to claim 1, or a pharmaceutically acceptable salt thereof.

8. A process for selective hydrogenation of alkenes or alkynes in the presence of the cobalt complex compound according to claim 1, as catalysts, the process comprising mixing alkyne/alkene, amino-borane, the cobalt complex compound and methanol, followed by stirring for a period in the range of 10 to 14 h at a temperature range of 50 to 80° C. to obtain the desired alkene/alkane.

9. The process as claimed in claim 8, wherein said alkyne/alkene is an alkyne selected from the group consisting of internal alkyne or terminal alkyne, or is a terminal alkene; and said cobalt complex compound is selected from compounds 1A, 1B, 1C, 1D, 2A, 2B, 2C or 2D.

* * * * *